United States Patent [19]

Bergström et al.

[11] 4,363,806
[45] Dec. 14, 1982

[54] PHARMACEUTICAL COMPOSITION

[75] Inventors: Karl O. Bergström; Jan Ulmius, both of Lund; Bo L. T. Wenngren, Malmö, all of Sweden

[73] Assignee: Aktiebolaget Draco, Lund, Sweden

[21] Appl. No.: 272,881

[22] Filed: Jun. 12, 1981

[30] Foreign Application Priority Data

Jun. 19, 1980 [SE] Sweden .................... 8004580

[51] Int. Cl.³ ........................................ A61K 31/58
[52] U.S. Cl. ................................................ 424/241
[58] Field of Search ..................................... 424/241

[56] References Cited

U.S. PATENT DOCUMENTS

| | | | |
|---|---|---|---|
| 3,395,028 | 7/1968 | Mackles | 106/8 |
| 4,198,403 | 4/1980 | Alvarez | 424/241 |
| 4,284,630 | 8/1981 | Yu et al. | 424/241 |

FOREIGN PATENT DOCUMENTS

| | | | |
|---|---|---|---|
| 1792410 | 11/1971 | Fed. Rep. of Germany | 424/241 |
| 2347243 | 10/1974 | Fed. Rep. of Germany | 424/241 |
| 2514873 | 10/1976 | Fed. Rep. of Germany | 424/241 |
| 2714065 | 10/1978 | Fed. Rep. of Germany | 424/241 |
| 2207692 | 6/1974 | France | 260/239.55 C |
| 2342061 | 9/1977 | France . | |
| 53-56315 | 5/1978 | Japan | 424/241 |
| 1080994 | 8/1967 | United Kingdom | 424/241 |
| 1541463 | 2/1979 | United Kingdom | 424/241 |

*Primary Examiner*—Elbert L. Roberts
*Attorney, Agent, or Firm*—Brumbaugh, Graves, Donohue & Raymond

[57] ABSTRACT

A pharmaceutical steroid composition for topical application producing a minimum of skin irritating effects. The composition comprises a corticosteroid in a multiple emulsion vehicle.

A process for the preparation of the composition.

8 Claims, No Drawings

PHARMACEUTICAL COMPOSITION

DESCRIPTION

1. Technical Field

The present invention is concerned with pharmaceutical compositions for topical application containing a corticosteroid as the active ingredient.

The object of the present invention is to provide a composition which produces a minimum of skin irritating effects.

A further object of the invention is to provide a composition with good bioavailability and good cosmetic properties.

2. Background Art

The usual administration form for topical corticosteroids is a cream or lotion, preferably an oil in water (O/W) emulsion, because of good cosmetic properties. However, most corticosteroids have exceedingly low solubilities in water, petrolatum or mineral oils. Many different solvents (e.g. propylene glycol) are in use to increase the solubility of the corticosteroids in the vehicles. One major disadvantage of using high concentrations of solvents in the vehicles, in some bases up to 50-60%, is the risk of skin irritation effects.

DISCLOSURE OF THE INVENTION

In order to minimize the skin irritation effects of the composition, the vehicle should contain as small amount of solvent as possible to dissolve the steroid.

The smallest amount of solvent is needed when the solvent is in neat form, and it is therefore necessary to compart the steroid solution in the vehicle to avoid mixing and diluting with the rest of the ingredients.

In order to get maximal drug diffusion into the skin from a vehicle the drug should be at a saturation concentration in the vehicle employed to administer the drug to the skin surface.

The present invention provides a system for realizing the above mentioned demands in the form of a multiple emulsion where the oil globules of the disperse phase contain smaller globules of a corticosteroid solution phase dispersed within them. More particular, the present invention provides a pharmaceutical composition for topical application comprising a topically active antiinflammatory corticosteroid in a multiple emulsion in which the continuous phase is aqueous and the primary disperse phase is an oil phase in which a hydrophilic phase containing the steroid in saturated solution is dispersed.

As solvent phase forming material any good solvent which is not miscible with the oil phase can be used for the steroid in question. Preferably glycols, e.g. propylene glycol, butandiols, polyethylene glycols are used. The amount of these solvent phase forming materials depends on the solubility properties of the steroid, but is usually 0.2-5% (w/w) of the complete composition.

As the oil phase forming material a fat with suitable viscosity range is used, for example petrolatum or mixtures of petrolatum and animal oils, such as wool grease, mixtures of petrolatum and vegetable oils, such as peanut oil, olive oil, mixtures of petrolatum and mineral oils, such as paraffin oil, isopropylmyristate, isopropylpalmitate and triglycerides, mixtures of petrolatum and synthetic oils, such as silicone oils. The amount of these oil phase forming materials depends on the desired fat content of the multiple emulsion but is generally in the range 10-50% (w/w) of the multiple emulsion.

The continuous phase consists of 40-80% (w/w) of water, and a water-soluble emulsifier. This phase may also consist of a fatty alcohol, such as cetostearyl alcohol. The emulsifier to be used for the formation of the dispersion of the solution of steroid in the oil phase should have such an appropriate hydrophilic-lipophilic balance that the oil phase used can form the dispersion medium of the solution in the oil emulsion. Beeswax, sorbitan fatty esters and monoglycerides are preferably used as emulsifiers. The amount of oil-soluble emulsifier is usually 1-20% (w/w) of the amount of the oil phase.

The water soluble emulsifier is an emulsifier having a hydrophilic-lipophilic balance at which the oil phase can form the dispersed phase of the oil in water emulsion. Preferably a non-ionic emulsifier, for example cetomacrogol 1000 [$CH_3(CH_2)_mO(CH_2OCH_2)_n$—$CH_2OH$ where m may be 15 or 17 and n may be 19 to 23], is used. The amount of the water-soluble emulsifier to be added is typically in the range 1-20% (w/w) of the amount of the oil phase described above.

The corticosteroid may be any topically active corticosteroid, such as budesonide, hydrocortisone, hydrocortisone acetate, triamcinolone acetonid, fluocinolone acetonide or betamethasone 17-valerate.

The preparation of the topical steroid composition starts with dissolving the steroid in the most suitable solvent.

The steroid solution in oil emulsion is then prepared from the oil phase forming material and the steroid solution. The oil-soluble emulsifier and the steroid solution is added to the oil phase forming material which is heated and agitated to form a steroid solution in oil emulsion. Then this steroid solution in oil emulsion is added to an aqueous solution prepared by dissolving the water-soluble emulsifier in water to form the multiple emulsion during heating and agitation.

WORKING EXAMPLES

EXAMPLE 1

| I. | Internal steroid solution phase | |
|---|---|---|
|  | Budesonide | 0.025 gram |
|  | Propylene glycol | 2.5 gram |
| II. | Oil phase | |
|  | Petrolatum | 21.25 gram |
|  | Bees wax | 1.25 gram |
| III. | External water phase | |
|  | Cetostearyl alcohol | 3.0 gram |
|  | Cetomacrogol 1000 | 2.0 gram |
|  | Distilled water | 70.0 gram |

The budesonide was dissolved in propylene glycol during heating to 70° C. making up solution (I). (I) was added to (II) at 70° C. and the mixture was subjected to agitation by a homomixer to prepare a steroid solution in oil emulsion. This emulsion was added to (III) preheated to 70° C. during agitation by a homomixer resulting in the multiple emulsion. After cooling to room temperature during gentle agitation a soft white shiny cream was obtained.

EXAMPLE 2

| I. | Internal steroid solution phase | |
|---|---|---|
|  | Budesonide | 0.025 gram |
|  | 1.2 Butandiol | 2.5 gram |
| II. | Oil phase | |

-continued

|     |                         |            |
|-----|-------------------------|------------|
|     | Petrolatum              | 21.25 gram |
|     | Beeswax                 | 1.25 gram  |
| III.| External water phase    |            |
|     | Cetostearyl alcohol     | 3.0 gram   |
|     | Cetomacrogol 1000       | 2.0 gram   |
|     | Distilled water q.s. ad | 100 gram   |

EXAMPLE 3

| I.  | Internal steroid solution phase |            |
|-----|---------------------------------|------------|
|     | Budesonide                      | 0.025 gram |
|     | Polyethylene glycol 400         | 2.0 gram   |
| II. | Oil phase                       |            |
|     | Petrolatum                      | 21.25 gram |
|     | Beeswax                         | 1.25 gram  |
| III.| External water phase            |            |
|     | Cetostearyl alcohol             | 3.0 gram   |
|     | Cetomacrogol 1000               | 2.0 gram   |
|     | Distilled water q.s. ad         | 100 gram   |

EXAMPLE 4

| I.  | Internal steroid solution phase |            |
|-----|---------------------------------|------------|
|     | Budesonide                      | 0.025 gram |
|     | Propylene glycol                | 2.5 gram   |
| II. | Oil phase                       |            |
|     | Petrolatum                      | 30 gram    |
|     | Mineral oil                     | 10 gram    |
|     | Sorbitan monooleat (Span 80)    | 5 gram     |
| III.| External water phase            |            |
|     | Cetostearyl alcohol             | 8 gram     |
|     | Cetomacrogol 1000               | 3 gram     |
|     | Distilled water q.s. ad         | 100 gram   |

EXAMPLE 5

| I.  | Internal steroid solution phase |            |
|-----|---------------------------------|------------|
|     | Budesonide                      | 0.025 gram |
|     | Propylene glycol                | 2.5 gram   |
| II. | Oil phase                       |            |
|     | Miglycol 812                    | 10 gram    |
|     | Petrolatum                      | 10 gram    |
|     | Beeswax                         | 1.5 gram   |
| III.| External water phase            |            |
|     | Cetanol                         | 5 gram     |
|     | Stearol                         | 5 gram     |
|     | Cetomacrogol 1000               | 3 gram     |
|     | Distilled water q.s. ad         | 100 gram   |

EXAMPLE 6

| I.  | Internal steroid solution phase |            |
|-----|---------------------------------|------------|
|     | Hydrocortisone                  | 0.1 gram   |
|     | Propylene glycol                | 5.0 gram   |
| II. | Oil phase                       |            |
|     | Petrolatum                      | 21.25 gram |
|     | Beeswax                         | 2.5 gram   |
| III.| External water phase            |            |
|     | Cetostearyl alcohol             | 5 gram     |
|     | Cetomacrogol                    | 2 gram     |
|     | Distilled water q.s. ad         | 100 gram   |

EXAMPLE 7

| I.  | Internal steroid solution phase |            |
|-----|---------------------------------|------------|
|     | Triamcinolone acetonid          | 0.025 gram |

-continued

|     |                         |            |
|-----|-------------------------|------------|
|     | Propylene glycol        | 2.5 gram   |
| II. | Oil phase               |            |
|     | Petrolatum              | 21.25 gram |
|     | Beeswax                 | 2.5 gram   |
| III.| External water phase    |            |
|     | Cetostearyl alcohol     | 5 gram     |
|     | Cetomacrogol 1000       | 2 gram     |
|     | Distilled water q.s. ad | 100 gram   |

EXAMPLE 8

| I.  | Internal steroid solution phase |            |
|-----|---------------------------------|------------|
|     | Fluocinolone acetonide          | 0.025 gram |
|     | Propylene glycol                | 2.5 gram   |
| II. | Oil phase                       |            |
|     | Petrolatum                      | 21.25 gram |
|     | Beeswax                         | 2.5 gram   |
| III.| External water phase            |            |
|     | Cetostearyl alcohol             | 5 gram     |
|     | Cetomacrogol 1000               | 2 gram     |
|     | Distilled water q.s. ad         | 100 gram   |

EXAMPLE 9

| I.  | Internal steroid solution phase |            |
|-----|---------------------------------|------------|
|     | Betamethasone-17 Valerate       | 0.025 gram |
|     | Propylene glycol                | 2.5 gram   |
| II. | Oil phase                       |            |
|     | Petrolatum                      | 21.25 gram |
|     | Beeswax                         | 2.5 gram   |
| III.| External water phase            |            |
|     | Cetostearyl alcohol             | 5 gram     |
|     | Cetomacrogol 1000               | 2 gram     |
|     | Distilled water q.s. ad         | 100 gram   |

PHARMACOLOGICAL TEST

Irritation studies

As mentioned above maximal drug diffusion into the skin is obtained when the steroid is at saturation concentration in the vehicle. For conventional o/w creams with a large water phase (e.g. 70%) this means that the propylene glycol content must be 35% or higher in order to dissolve the steroid completely. With such high propylene glycol concentrations there is a risk for skin irritation. (Hannuksela et al., Contact Dermatitis 1, 112 (1975). Conventional o/w placebo creams with propylene content from 5 to 35% was tested using the chamber test method with an exposition time of 24 hours. Out of 96 tested persons 72 gave no reactions at all. Reactions with weak redness without infiltrations were observed 48 hours after application for the rest according to:

| % propylene glycol | 5 | 10 | 15 | 20 | 35 |
|--------------------|---|----|----|----|----|
| Number reactions   | 2 | 1  | 5  | 5  | 10 |

It is evident that the risk for skin irritation increases with increasing propylene glycol content. In a multiple emulsion cream according to this invention with an outer water phase as large as in a conventional o/w cream (70%) the propylene glycol content is below 5% (typically 2-3%) to dissolve the same amount of steroid. The risk for skin irritation is accordingly much lower than in a conventional o/w cream where a large amount of propylene glycol is needed to dissolve the steroid.

Best Mode Of Carrying Out The Invention

In the preferred composition the steroid is 16α,17α-(2'-hydrogen-2'-n-propyl)methylenedioxypregna-1,4-diene-11,21-diol-3,20-dione(budesonide) and the solvent propylene glycol.

We claim:

1. A pharmaceutical composition for topical application comprising a topically active anti-inflammatory corticosteroid in a multiple emulsion in which the continuous phase is aqueous and the primary disperse phase is an oil phase in which a hydrophilic phase containing the steroid in saturated solution is dispersed.

2. A composition according to claim 1 wherein the corticosteroid is 16α,17α-(2'-hydrogen-2'-n-propyl)methylenedioxypregna-1,4-diene-11,21-diol-3,20-dione.

3. A composition according to claim 1 wherein the steroid is dissolved in propylene glycol.

4. A composition according to claim 1 wherein the amount of steroid solvent is between 0.2 and 5% (w/w) of the complete composition.

5. A process for preparing a pharmaceutical steroid composition for topical application which is a multiple emulsion characterized in dissolving a topically active anti-inflammatory corticosteroid, combining the steroid solution together with an oil-soluble emulsifier with an oil-phase forming material, and thereafter combining this steroid solution in oil emulsion with an aqueous solution prepared by dissolving a water-soluble emulsifier in water or a mixture of water and a fatty alcohol to form a multiple emulsion.

6. A process according to claim 5 characterized in that the corticosteroid is 16α,17α-(2'-hydrogen-2'-n-propyl)methylenedioxypregna-1,4-diene-11,21-diol-3,20-dione.

7. A process according to claim 5 characterized in that the steroid is dissolved in propylene glycol.

8. A process according to claim 5 characterized in that the amount of steroid solvent is between 0.2 and 5% (w/w) of the complete composition.

* * * * *